United States Patent
Fujimaki et al.

(10) Patent No.: US 7,449,701 B2
(45) Date of Patent: Nov. 11, 2008

(54) PARTICLE BEAM IRRADIATION EQUIPMENT AND PARTICLE BEAM IRRADIATION METHOD

(75) Inventors: Hisataka Fujimaki, Hitachinaka (JP); Koji Matsuda, Hitachi (JP); Masaki Yanagisawa, Hitachi (JP); Hiroshi Akiyama, Hitachiohta (JP)

(73) Assignee: Hitachi, Ltd., Tokyo (JP)

( * ) Notice: Subject to any disclaimer, the term of this patent is extended or adjusted under 35 U.S.C. 154(b) by 0 days.

(21) Appl. No.: 10/822,767

(22) Filed: Apr. 13, 2004

(65) Prior Publication Data

US 2004/0200983 A1 Oct. 14, 2004

(30) Foreign Application Priority Data

Apr. 14, 2003 (JP) ............................. 2003-109062

(51) Int. Cl.
 *A61N 5/00* (2006.01)
 *H01J 33/00* (2006.01)

(52) U.S. Cl. .................... 250/492.3; 250/505.1

(58) Field of Classification Search .............. 250/492.3, 250/505.1

See application file for complete search history.

(56) References Cited

U.S. PATENT DOCUMENTS

| | | | | |
|---|---|---|---|---|
| 4,095,114 A | * | 6/1978 | Taumann | 250/505.1 |
| 4,736,106 A | * | 4/1988 | Kashy et al. | 250/396 ML |
| 4,952,814 A | * | 8/1990 | Huntzinger | 250/492.3 |
| 5,010,562 A | * | 4/1991 | Hernandez et al. | 250/492.3 |
| 5,440,133 A | * | 8/1995 | Moyers et al. | 250/492.3 |

FOREIGN PATENT DOCUMENTS

| | | |
|---|---|---|
| JP | 7-51395 | 2/1995 |
| JP | 2001-170194 | 6/2001 |
| JP | 2001-212253 | 8/2001 |
| JP | 2003-135608 | 5/2003 |

OTHER PUBLICATIONS

Chu et al., "Instrumentation for Treatment of Cancer Using Proton and Light-Ion Beams." Review of Scientific Instruments, vol. 64, No. 8, pp. 2079-2083, Aug. 1993.

* cited by examiner

*Primary Examiner*—Jack I Berman
(74) *Attorney, Agent, or Firm*—Dickstein Shapiro LLP (57) ABSTRACT

Particle beam irradiation equipment and a method of adjusting irradiation nozzle, which can ensure a long range and high dose uniformity at any field size are provided. The particle beam irradiation equipment comprises charged particle beam generation equipment and an irradiation nozzle for irradiating a charged particle beam extracted from the charged particle beam generation equipment to an irradiation target. The irradiation nozzle comprises a first scatterer device including a first scatterer for spreading out the charged particle beam into a Gaussian-like distribution, and multiple stages of second scatterer devices including second scatterers for producing a uniform intensity distribution of the charged particle beam having been spread out into a Gaussian-like distribution by the first scatterer. For forming irradiation fields having sizes different from each other, the second scatterer devices are disposed downstream of the first scatterer device in the direction of travel of the charged particle beam at the spacing depending on the difference in the field size.

30 Claims, 6 Drawing Sheets

PARTICLE BEAM IRRADIATION EQUIPMENT AND PARTICLE BEAM IRRADIATION METHOD

BACKGROUND OF THE INVENTION

1. Field of the Invention

The present invention relates to particle beam irradiation equipment. More particularly, the present invention relates to particle beam irradiation equipment, which is suitably applied to particle beam treatment for irradiating a charged particle beam of, e.g., proton ions or carbon ions, to a tumor for treatment, material irradiation equipment for irradiating a charged particle beam to materials, food irradiation equipment for irradiating a charged particle beam to foods, and radio isotope producing equipment utilizing a charged particle beam, and also relates to a method of adjusting irradiation field producing equipment used in the particle beam irradiation equipment.

2. Description of the Related Art

Known particle beam treatment equipment comprises charged particle beam generation equipment, an ion beam transport system, and rotating irradiation equipment. The charged particle beam generation equipment includes a synchrotron (or a cyclotron) as an accelerator. A charged particle beam accelerated by the synchrotron up to a level of setting energy reaches the rotating irradiation equipment through the ion beam transport system (i.e., a first ion beam transport system). The rotating irradiation equipment comprises an ion beam transport system within the irradiation equipment (i.e., a second ion beam transport system), irradiation field producing equipment, and a rotating apparatus (rotating gantry) for rotating both the second ion beam transport system and the irradiation field producing equipment in union with each other. After passing the second ion beam transport system, the ion beam is irradiated to a tumor or cancer in the patient body from the irradiation field producing equipment.

The irradiation field producing equipment has the functions of shaping the ion beam from the charged particle beam generation equipment in match with a three-dimensional shape of the tumor, as an irradiation target, to form an irradiation field, and adjusting the dose in the irradiation field. As a method of making irradiation at desired dose in match with the shape of the irradiation target, there is known a double scattering method of producing a uniform dose field by using two types of scatterers, which are arranged in spaced relation in the axial direction of the ion beam, based on a phenomenon that a dose distribution of the ion beam after passing a scatterer becomes substantially a Gaussian distribution (see, e.g., Non-patent Reference 1: "REVIEW OF SCIENTIFIC INSTRUMENTS", VOLUME 64, NUMBER 8 (AUGUST 1993) P2079-2083).

With the double scattering method, more specifically, the ion beam is first spread into a Gaussian-like distribution by one scatterer (first scatterer) arranged in the upstream side in the direction of travel of the ion beam, and is then adjusted so as to have a uniform does distribution by the other scatterer (second scatterer) arranged in the downstream side in the direction of travel of the ion beam. In medical applications where the ion beam is irradiated to cancer, particularly, it has been strongly demanded as a recent tendency to keep high dose uniformity, to increase the size of the irradiation field to be adaptable for a variety of tumor shapes in the patient bodies, and to increase the penetration depth in the patient body.

In the double scattering method, arranging the scatterers at positions as near as possible to the most upstream side is effective in decreasing the thickness of each of the first and second scatterers to reduce the range loss, and in extending the range to increase the penetration depth in the patient body. While the first scatterer is usually arranged near the most upstream side in the irradiation field producing equipment, the second scatterer is also preferably arranged, from the standpoint of increasing the range length, at a position as near as possible to the most upstream side so that the distance between the first and second scatterers is minimized. On the other hand, in the double scattering method, if a deviation occurs between an axis along which the ion beam travels and the center position of the second scatterer, dose uniformity deteriorates depending on the deviation to a larger extent as the distance between the first and second scatterers decreases. From the standpoint of improving dose uniformity, therefore, the second scatterer is preferably arranged at a position as near as possible to the most downstream side so that the distance between the first and second scatterers is maximized.

As a result, in design of the known irradiation field producing equipment, an optimum mount position of the second scatterer is decided in consideration of balance between a longer range and higher dose uniformity. However, when an available maximum field size is increased in the equipment responsive to the need for a larger size of the irradiation field as mentioned above, a proper mount position of the second scatterer in the case of producing a comparatively large field size greatly differs from the proper mount position thereof in the case of producing a comparatively small field size. Accordingly, it has been difficult to always realize irradiation with a long range and high dose uniformity regardless of the field size.

SUMMARY OF THE INVENTION

It is an object of the present invention to provide particle beam irradiation equipment and a particle beam irradiation method, which can provide a long range of a charged particle beam in the patient body and ensure high dose uniformity at any irradiation field size.

To achieve the above object, the present invention is featured in placing a plurality of second scatterers, through which a charged particle beam passes after having passed a first scatterer, in a passage region of the charged particle beam at one of a first position in the direction of travel of the charged particle beam and a second position downstream of the first position in the direction of travel of the charged particle beam.

Since the second scatterers can be optionally placed in the first position and the second position in the direction of travel of the charged particle beam, it is possible to change the position, at which the second scatterer is placed, depending on the size of an irradiation field to be formed. At any field size, therefore, a long range of the charged particle beam can be obtained in the patient body and higher dose uniformity can be ensured in irradiation. For example, when a comparatively large irradiation field is formed, the second scatterer is placed at the first position, and when a comparatively small irradiation field is formed, the second scatterer is placed at the second position. In either case, the second scatterer can be placed at an optimum position in consideration of balance between a longer range and higher dose uniformity. As a result, irrespective of the field size, the irradiation of the charged particle beam can be realized with a long range and high dose uniformity over the whole of the formable irradiation field.

Preferably, plural stages of second scatterer devices for forming the irradiation fields having sizes different from each other are disposed downstream of the first scatterer device in the direction of travel of the charged particle beam, and the spacing between the positions where the second scatterer devices are placed is set depending on the difference in the field size.

DESCRIPTION OF THE PREFERRED EMBODIMENTS

Embodiments of the present invention will be described in detail below with reference to the drawings.

First Embodiment

Figure 2:
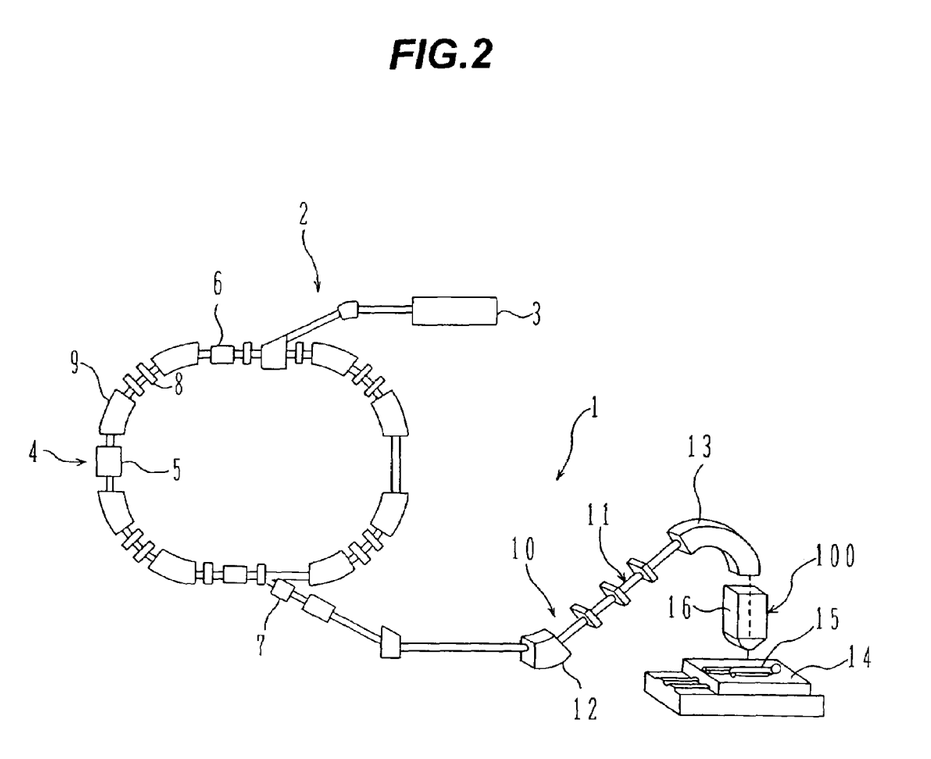
FIG. 2 is a schematic view showing a general construction of the particle beam irradiation equipment according to the first embodiment of the present invention.

Particle beam irradiation equipment (particle beam treatment equipment) as one preferable embodiment of the present invention will be described below with reference to FIG. 2. Particle beam irradiation equipment 1 of this embodiment comprises charged particle beam generation equipment 2 and irradiation field producing equipment (irradiation nozzle) 100. The charged particle beam generation equipment 2 comprises an ion source (not shown), a pre-accelerator 3, and a synchrotron 4. Ions (e.g., proton ions (or carbon ions)) generated by the ion source are accelerated by the pre-accelerator 3 (e.g., a linear accelerator (LINAC)). An ion beam (charged particle beam) emitted from the pre-accelerator 3 enters a synchrotron 4. The ion beam is accelerated in the synchrotron 4 by being given with energy in the form of RF-power applied from an RF-accelerating cavity 5. After energy of the ion beam circulating in the synchrotron 4 has been increased up to a setting level, a radio frequency wave is applied to the circulating ion beam from an RF-applying device 6 for beam extraction. With the application of the radio frequency wave, the ion beam circulating within a separatrix in phase space is forced to transit outside the separatrix in phase space and to exit from the synchrotron 4 through an electrostatic deflector (for beam extraction) 7. At the time of extracting the ion beam, currents supplied to magnets, such as quadrupole magnets 8 and bending magnets 9, disposed in the synchrotron 4 are held at setting values, and the separatrix in phase space is also held substantially constant. The extraction of the ion beam from the synchrotron 4 is stopped by stopping the application of the RF-power to the RF-applying device 6.

The ion beam extracted from the synchrotron 4 reaches the irradiation nozzle 100, serving as the irradiation field producing equipment, through the ion beam transport system 10. An inverted U-shaped portion 11, as a part of the ion beam transport system 10, and the irradiation nozzle 100 are installed within a rotating gantry (not shown). The inverted U-shaped portion 11 includes bending magnets 12, 13. The ion beam is irradiated from the irradiation nozzle 100 to a tumor K (see FIG. 1) in the body of a patient 15 lying on a treatment couch (bed) 14.

Figure 1:
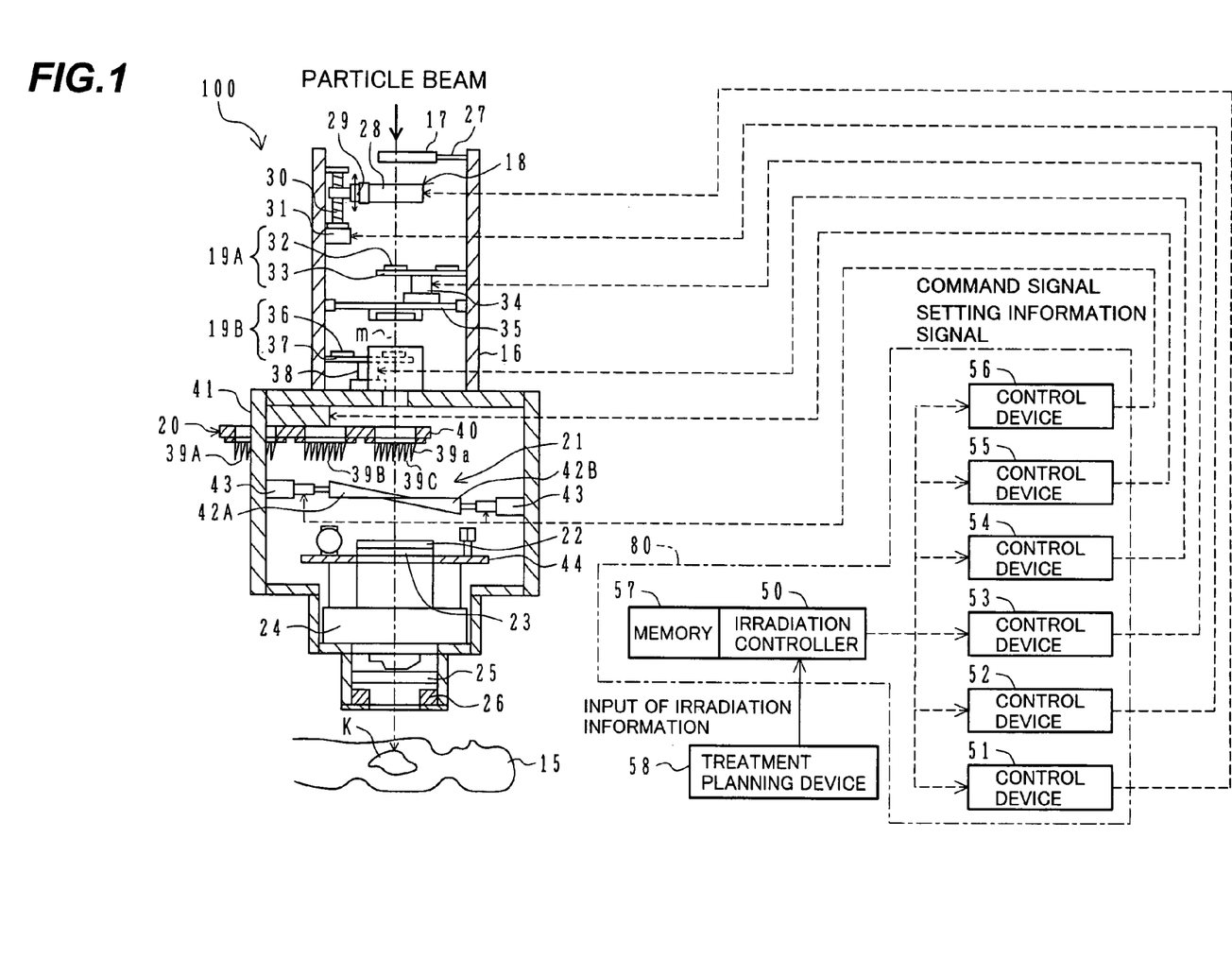
FIG. 1 is a vertical sectional view showing a detailed construction of irradiation field producing equipment provided in particle beam irradiation equipment according to a first embodiment of the present invention.

A detailed construction of the irradiation nozzle 100 used in the particle beam irradiation equipment 1 will be described below with reference to FIG. 1.

The irradiation nozzle 100 has a casing 16 mounted to the inverted U-shaped portion 11. Within the casing 16, a beam profile monitor 17, a first scatterer device 18, a second scatterer device 19, a Bragg peak spreading-out device (SOBP (spread-out bragg peak) producing device) 20, a range adjustment device 21, a dose monitor 22, a flatness monitor 23, a block collimator 24, a bolus 25, and a patient collimator 26 are successively arranged in this order from the upstream side in the direction of travel of the ion beam. The second scatterer device 19 includes a second scatterer device (second scatterer device for large field size) 19A and a second scatterer device (second scatterer device for small field size) 19B.

The beam profile monitor 17 measures the position of an incident ion beam, and it is fixed to the housing 16 through a support member 27.

The first scatterer device 18 has the function of spreading an irradiation area perpendicular to the direction of travel of the ion beam, and includes a plurality of scatterers (first scatterers) 28 arranged in the direction of travel of the ion beam. Materials of each first scatterer 28 are generally selected from among substances having large atomic numbers, such as lead and tungsten, which have small energy losses with respect to the scattering rate. The scattering rate is set in this embodiment by a method of placing a plurality of flat plates one above another, which are each made of one kind or plural kinds of materials, and adjusting the thickness of the first scatterer device 18 on the binary basis. As an alternative, the scattering rate may be set by a method of combining a set of two wedge-shaped blocks with each other, and driving the wedge-shaped blocks so that the thickness of the first scatterer device 18 is continuously adjusted. These methods are in common in the point of changing the thickness and the material of each first scatterer. The scatterers 28 of the first scatterer device 18 are arranged on an axis along which the ion beam travels (hereinafter referred to as a "beam axis") m, though not described in detail here, so as to achieve the setting thickness in accordance with a driving command signal from a control device 51 described later.

Further, the scatterers 28 are each mounted to a support member 29 having a screwed hole formed therein, and a ball screw 30 is meshed with the screwed hole of the support member 29. Each scatterer 28 is provided with a scatterer shifting device (not shown) for shifting the relevant scatterer 28 in the direction perpendicular to the beam axis m. An upper end of the ball screw 30 is rotatably mounted to the casing 16. A lower end of the ball screw 30 is coupled to a rotary shaft of a motor 31 (e.g., an AC servo motor or a stepping motor) mounted to the casing 16. The first scatterer device 18 is allowed to move only in the vertical direction along the beam axis m under guide of a guide means (not shown), while it is restricted from rotating about the ball screw 30 by the guide means. With such a structure, the motor 31 and the ball screw 30 constitute a device for moving the scatterers 28 (i.e., a first scatterer moving device or a linear actuator). In addition, an encoder (not shown) is coupled to the rotary shaft of the motor 31. The above-described movement of the first scatterer device 18 in the direction of travel of the ion beam is intended to mainly perform fine adjustment of the scatter strength of the ion beam and is allowed within a comparatively small distance. In other words, the first scatterer device 18 does not essentially have the functions (of providing a long range and higher dose uniformity depending on the irradiation field) similar to those ones intended by the selective use of second scatterer devices 19A, 19B (described below).

The second scatterer devices 19A, 19B modulate the ion beam, which has been spread out into a Gaussian distribution by the first scatterer device 18, to produce a uniform dose distribution, and one of the two scattering functions of those second scatterer devices is selectively employed. The second scatterer devices 19A, 19B are arranged in two stages in the direction of travel of the ion beam such that the second scatterer device 19A is disposed on the upstream side and used in the case where the size of the irradiation field to be formed is large, whereas the second scatterer device 19B is disposed on the downstream side and used in the case where the size of the irradiation field to be formed is small.

The second scatterer device 19A includes a plurality of second scatterers (scatterers for large field size) 32 used in the case where the field size is comparatively large. The second scatterers 32 are each formed of plural kinds of materials with plural values of thickness to provide equal energy losses and different scatter strengths of particles at positions where the particles pass (i.e., to provide relatively high scatter strength in the central side and relatively low scatter strength in the radially outer peripheral side) so that the intensity of the ion beam spread out into a Gaussian distribution by the first scatterer device 18 becomes uniform. Each scatterer 32 may be of, e.g., a dual ring structure or a Contoured structure in which proportions of used materials are changed in a stepwise manner.

Further, a plurality of scatterers 32 (five scatterers 32a to 32e in this embodiment) are circumferentially disposed on a scatterer mount table (i.e., a first table or an upstream table) 33 having a circular (or substantially disk-like) shape. In a portion of the table 33 where no scatterers 32 are disposed, a blank port (opening) 33a (see FIG. 3 described later) is formed to allow the ion beam scattered by the first scatterer device 18 to pass through the second scatterer device 19A as it is. The table 33 is rotatably supported, through a table moving device 34, by a support member 35 fixed to the casing 16. For the purpose of making irradiation at high efficiency and high accuracy, with the rotation of the table 33 by the table moving device 34, one of the plural scatterers 32a to 32e is selected to be positioned on the beam axis to perform desired scattering or the blank port 33a is positioned on the beam axis, thus causing the ion beam to pass without scattering.

The second scatterer device 19B includes a plurality of second scatterers (scatterers for small field size) 36 used in the case where the field size is comparatively small. Depending on the difference between the large field size formed by the second scatterers 32 of the second scatterer device 19A and the small field size formed by the second scatterers 36 of the second scatterer device 19B, the second scatterer device 19B is disposed at a position spaced downstream of the second scatterer device 19A by a preset distance (e.g., about 200 mm to several hundreds mm).

Each second scatterer 36 of the second scatterer device 19B is basically identical to each second scatterer 32 of the second scatterer device 19A. Because of forming the small field size, however, the second scatterer 32 generally has a thickness and a radial size different from those of the second scatterer 32 for the large field size. Similarly to the second scatterers 32, in this embodiment, five scatterers 36a to 36e are circumferentially disposed as the second scatterers 32 on a scatterer mount table (i.e., a second table or a downstream table) 37 having a circular (or substantially disk-like) shape. Also, a blank port (opening) 37a (see FIG. 3 described below) is formed in the table 37 to allow the ion beam to pass through the second scatterer device 19B as it is. Similarly to the table 33, the table 37 is rotatably supported to the casing 16. With the rotation of the table 37 by the table moving device 38, one of the plural second scatterers 36a to 36e and the blank port 37a is selected to be positioned on the beam axis so that irradiation is made at high efficiency and high accuracy.

Figure 3:
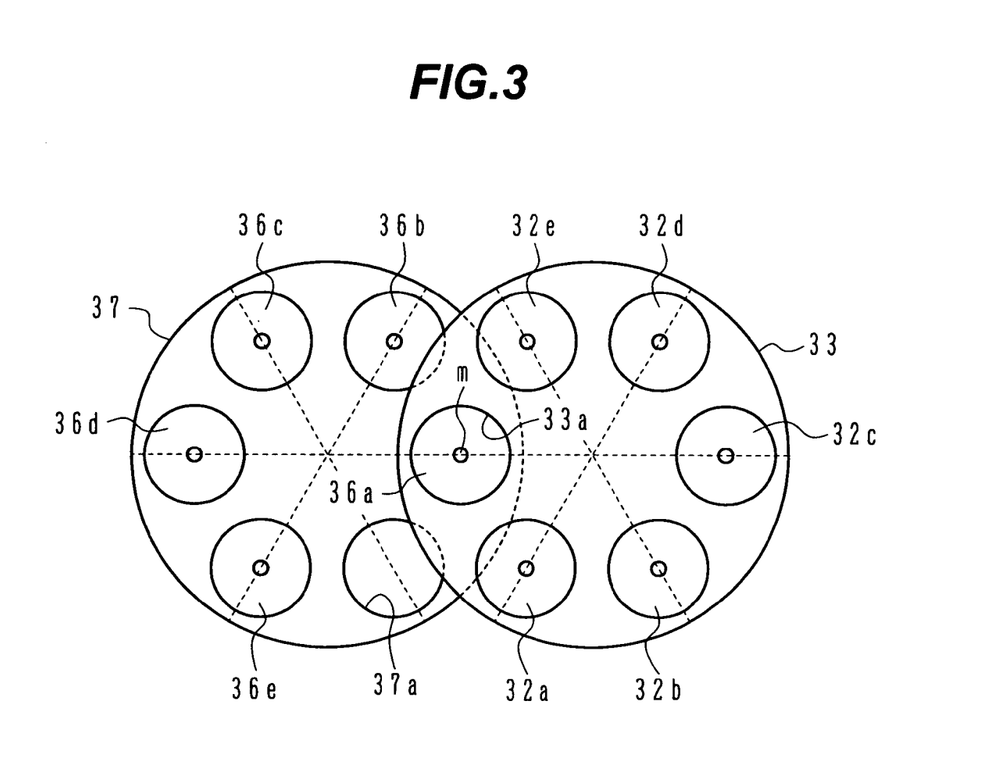
FIG. 3 shows the positional relationship between tables on which second scatterer devices shown in FIG. 1 are mounted, looking from the upstream side in the direction of travel of an ion beam.

FIG. 3 shows the positional relationship between the tables 33 and 37 of the second scatterer devices 19A, 19B constructed as described above, looking from the upstream side in the direction of travel of the ion beam. As shown, the scatterer mount tables 33, 37 are arranged such that the second scatterers 32a to 32e and the blank port 33a circumferentially mounted on the table 33 are aligned with the second scatterers 36a to 36e and the blank port 37a circumferentially mounted on the table 37 when they are selectively positioned on the beam axis m. FIG. 3 shows the case in which the second scatterer 36a of the second scatterer device 19B is selected as a second scatterer for modulating the ion beam spread out into a Gaussian distribution by the first scatterer device 18 into a uniform dose distribution. In other words, the table 33 is rotated to position the blank port 33a of the second scatterer device 19A on the beam axis m, and the table 37 is rotated to position the second scatterer 36a of the second scatterer device 19B on the beam axis m.

The above description is made in connection with an example in which the tables 33, 37 are circular in shape and rotated to select one of the second scatterers and the blank port, but the present invention is not limited to such an arrangement. As an alternative, for example, each table may be rectangular in shape and moved to slide in biaxial directions orthogonal to each other on a plane perpendicular to the beam axis under control of a table controller.

The SOBP producing device 20 increases the energy distribution width of the ion beam to spread the dose distribution along the depth in the direction of travel of the ion beam, and it is also called, e.g., an SOBP filter, an energy modulating device, or a beam energy filter. In general, the SOBP producing device 20 is made of a substance having a small atomic number, such as a plastic material or aluminum, which has a small scattering rate with respect to the amount of energy loss, and is formed such that regions differing in thickness from each other are defined on a flat plane perpendicular to the direction of travel of the ion beam. The ion beam has a plurality of energy components after passing the regions with different values of thickness. The weight of each energy component is determined depending on the area of each region. A dose distribution having high uniformity in the direction of travel of the ion beam is formed with adjustment of the dose distribution through superimposition of those plural energy components.

In this embodiment, the SOBP producing device 20 is constituted as the so-called ridge filter, and includes three kinds of wedge structures 39A, 39B and 39C. The wedge structures 39A, 39B and 39C are each formed of an array of many wedge-shaped members (materials molded into wedge shapes) 39a extending toward the range adjustment device 21 (downward in this embodiment), each of the wedge-shaped members 39a having steps formed in both lateral surfaces thereof.

Figure 4:
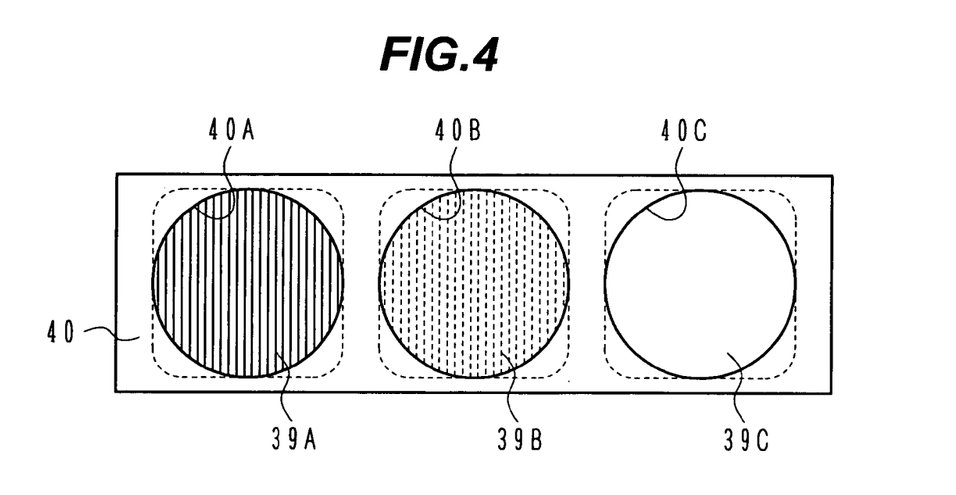
FIG. 4 is a plan view showing a detailed structure of wedge structures of an SOBP producing device shown in FIG. 1.

FIG. 4 is a plan view showing a detailed structure of the wedge structures 39A, 39B and 39C. The wedge structures 39A, 39B and 39C are mounted to a rectangular support member (table) 40 provided with corresponding through holes 40A, 40B and 40C. The table 40 is moved by a moving device (e.g., an AC servo motor) 41, which is mounted to the casing 16, so as to slide in the uniaxial direction (in the left-and-right direction in FIG. 1) in a plane perpendicular to the beam axis for proper selection of desired one of the wedge structures 39A, 39B and 39C. The wedge structures 39A, 39B and 39C are formed such that their wedge-shaped members differ from each other in, e.g., height of themselves and width and height of the steps. The wedge structures having. proper values of those parameters are selected depending on the beam energy incident upon the irradiation nozzle 100 and the SOBP width, and are mounted to the table 40 in advance. The SOBP width is decided depending on the length of the tumor K in the direction of travel of the ion beam.

The table 40 is not limited to the rectangular form, and it may have any suitable shape. For example, the arrangement may be modified such that a circular table is disposed perpendicularly to the beam axis, and a plurality of wedge structures are circumferentially arranged on the table, thus allowing the wedge structure to be selected (changed) with the rotation of the table.

Instead of the ridge filter described above, the SOBP producing device 20 may be constituted, for example, as a Range Modulator Wheel (rotating wheel) that is a propeller-like structure having blades each formed of a material processed into a stepped shape (the wheel being rotated in a plane perpendicular to the beam axis). In this case, the dose distribution in the direction of travel of the ion beam is adjusted to become uniform by taking an average of the superimposed energy components over time. That type of SOBP producing devices is described in detail, for example, in "REVIEW OF SCIENTIFIC INSTRUMENTS", VOLUME 64, NUMBER 8 (AUGUST 1993) P2074-2079).

Alternatively, without using the SOBP producing device 20, the dose distribution can also be adjusted by modulating the energy and intensity of the ion beam incident upon the irradiation nozzle 100.

The range adjustment device 21 reduces the range of the ion beam based on energy loss occurred during passage through a device material. In other words, the range adjustment device 21 serves as a device for adjusting the maximum penetration depth in the patient body, i.e., the range, by changing the energy loss depending on the cases, and it is also called a range shifter, a fine degrader, an energy degrader, etc. Generally, the range adjustment device 21 is made of a substance having a small atomic number, such as acrylic or ABS resin, which has a small scattering rate with respect to the amount of energy loss.

In this embodiment, the range adjustment device 21 comprises one set of two wedge-shaped blocks (energy absorbers) 42A, 42B arranged on both sides of the beam axis in opposed relation. The blocks 42A, 42B are moved respectively by block moving devices (e.g., AC servo motors) 43, 43, which are mounted to the casing 16, so as to slide in the uniaxial direction (in the left-and-right direction in FIG. 1) in a plane perpendicular to the beam axis m. As a result, the thickness of an overlapped portion of the blocks 42A, 42B is continuously changed, whereby the thickness of the material through which the charged particles pass is changed.

Instead of using the wedge-shaped blocks described above, the range adjustment device 21 may be designed, for example, based on a method of placing a plurality of flat plates one above another, which are each made of one kind or plural kinds of materials, and adjusting the total thickness on the binary basis so as to set the amount of energy loss.

Further, the range adjustment device 21 is not always required. The function of the range adjustment device 21 can be replaced by increasing the thickness of the bolus 25 described later, and the range can also be adjusted by finely adjusting the energy of the incoming charged particle beam.

The dose monitor 22 measures the dose distribution within the formed irradiation field, and the flatness monitor 23 measures flatness of the dose distribution. These monitors 22, 23 are both disposed on a table-like support member 44.

The block collimator 24 roughly collimates the irradiation field, and it is mounted to the casing 16.

The bolus 25 adjusts the penetration depth of the ion beam in match with the maximum depth of the tumor K in the body of the patient 15 under treatment such that the ranges at various positions in a plane perpendicular to the direction of travel of the ion beam are adjusted to be matched with the shape of the tumor K, as the irradiation target, in the depth direction. The bolus 25 is also called a range compensator, an energy compensator, or simply a compensator. The bolus 25 is not employed in some cases, such as when irradiation is made from multiple directions or toward a particular treatment location.

The patient collimator 26 shapes the ion beam in match with the tumor shape in a planar direction perpendicular to the direction of travel of the ion beam. The patient collimator 26 is not employed in some cases depending on a particular treatment location.

The irradiation field formed by the irradiation nozzle 100 having the above-described construction dissipates energy in the tumor K in the body of the patient 15 under treatment, thereby forming a high dose region. While the first scatterer device 18 and the second scatterer devices 19A, 19B are arranged in the fixed order described above, the order in arrangement of the other components may be modified such that the SOBP producing device 20 and the range adjustment device 21 are disposed upstream of the first scatterer device 18, or between the first scatterer device 18 and the second scatterer devices 19A, 19B. Also, the bolus 25 and the patient collimator 26 are both disposed downstream of the second scatterer devices 19A, 19B, but the order in arrangement of those components may be reversed in some cases to the order described above.

The particle beam treatment equipment of this embodiment includes a control system 80 comprising an irradiation controller 50 and control devices 51 to 56. Instead of providing the irradiation controller 50 and the control devices 51 to 56 as individual units, the control system 80 may be designed as one unit to execute all the functions of the irradiation controller 50 and the control devices 51 to 56.

A memory 57 is associated with the irradiation controller 50 and stores irradiation condition information therein. Items of the irradiation condition information includes the thickness of the first scatterer 28 positioned in the ion beam passage region within the irradiation nozzle 100 (i.e., SC1 thickness), the position of the first scatterer 28 in the direction of travel of the ion beam (i.e., SC1 position), the thickness of the blocks 42A, 42B positioned in the ion beam passage region within the range adjustment device 21 (i.e., RS thickness), the type of the second scatterer device (19A or 19B) (i.e., SC2 table), and the type of the second scatterer 32, 36 to be positioned in the ion beam passage region (i.e., SC2 type). As listed in Table 1 given below, by way of example, the irradiation condition information is determined in advance corresponding to the size of the tumor K, as the irradiation target, in the direction perpendicular to the beam axis m (i.e., the field size or diameter), the position (i.e., the maximum field penetration depth or range) and the size of the tumor K in the direction of the beam axis (depth direction), and the ion beam energy incident upon the irradiation nozzle 100 (i.e., beam Eg). The relationships among the field size, the range (ion beam range inside the patient body), the energy of the incident ion beam, the thickness of the first scatterer, the position of the first scatterer, the block thickness of the range adjustment device, the type of the second scatterer mount table, and the type of the second scatterer are determined in advance based on calculations and experiments. Further, the correspondence between the range and the types of the wedge structures 39A, 39B and 39C prepared in the SOBP producing device 20 is also determined in advance and stored in the memory 57 as the irradiation condition information.

The operation of the thus-constructed particle beam irradiation equipment of this embodiment will be described below.

First, prior to positioning of the patient 15 relative to the irradiation nozzle 100, the irradiation controller 50 receives the treatment plan information (such as the field size, the range and the beam energy) for the patient 15 from the treatment planning device 58, and then stores the received treatment plan information in the memory 57 (alternatively, the irradiation controller 50 may determine the irradiation condition, such as the field size and the range, in accordance with the position and shape of the tumor K inputted from the treatment planning device 58 and then store the determined irradiation condition in the memory 57). By employing the field size (irradiation information), the range (range information), and the beam energy (beam energy information), which are stored in the memory 57 as the treatment plan information for the patient 15, the irradiation controller 50 selects the thickness of the first scatterer, the position of the first scat-

TABLE 1

| Field Size | Range | Beam Eg | SC1 Thickness | SC1 Position | RS Thickness | SC2 Table | SC2 Type |
|---|---|---|---|---|---|---|---|
| φ350 [mm] | 40 [mm] : | 100 [MeV] | 3 [mm] : | 70 [mm] : | 50 [mm] : | 1 (upstream) | 1-1 |
| | 90 [mm] 90 [mm] : | 150 [MeV] | 6 [mm] | 0 [mm] 50 [mm] : | 0 [mm] 60 | | |
| | 150 [mm] 150 [mm] : | 200 [MeV] | 10 [mm] | 0 [mm] 30 [mm] : | 0 [mm] : | | 1-2 |
| | : | 250 [MeV] | 15 [mm] | 0 [mm] 10 [mm] : | 0 [mm] : | | |
| φ200 [mm] | 40 [mm] : | 100 [MeV] | 2 [mm] | 0 [mm] 100 [mm] : | 0 [mm] 50 [mm] : | 2 (downstream) | 2-1 |
| | 90 [mm] 90 [mm] : | 150 [MeV] | 4 [mm] | 0 [mm] 80 [mm] : | 0 [mm] 60 [mm] : | | |
| | 150 [mm] 150 [mm] : | 200 [MeV] | 7 [mm] | 0 [mm] 60 [mm] : | 0 [mm] : | | 2-2 |
| | : | 250 [MeV] | 10 [mm] | 0 [mm] 30 [mm] : | 0 [mm] : | | |
| φ60 [mm] | 40 [mm] : | 100 [MeV] | 1 [mm] | 0 [mm] 100 [mm] : | 0 [mm] 50 [mm] : | 2 (downstream) | 2-3 |
| | 90 [mm] 90 [mm] : | 150 [MeV] | 2 [mm] | 0 [mm] 100 [mm] : | 0 [mm] 60 [mm] : | | |
| | 150 [mm] 150 [mm] : | 200 [MeV] | 3.5 [mm] | 0 [mm] 80 [mm] : | 0 [mm] : | | 2-4 |
| | : | 250 [MeV] | 5 [mm] | 0 [mm] 60 [mm] : | 0 [mm] 0 [mm] | | |

A treatment planning device 58 stores treatment plan information (such as the field size, the incident direction of the ion beam, the range in the incident direction, and the beam energy) for the patient 15 to be subjected to the treatment.

terer, the type of the second scatterer mount table, the type of the second scatterer, and the thickness of the energy absorber (thickness of the range adjustment device) from among the irradiation condition information that is listed, by way of example, in Table 1 and is also stored in the memory 57 in advance. For example, the type of the second scatterer mount table (i.e., the position of the second scatterer in the direction of travel of the ion beam) is selected based on the irradiation field information, and the position of the first scatterer and the type of the second scatterer are selected based on the beam energy information. The scatterer having a larger thickness is selected as the energy of the incident ion beam increases, and the energy absorber having a larger thickness is selected as the required range becomes shorter.

Then, the irradiation controller 50 outputs the information indicating the selected thickness of the first scatterer to the control device 51 along with a command signal. In accordance with the outputted thickness information, the control device 51 selects one or more scatterers 28 of the first scatterer device 18 so that the selected thickness is obtained. The control device 51 operates the corresponding scatterer moving device in accordance with the command signal and moves the selected scatterer 28 to be positioned on the beam axis m.

Further, the irradiation controller 50 outputs the position information of the first scatterer, along with a command signal, to the control device 52 for controlling the movement of the first scatterer. In accordance with the outputted position information, the control device 52 rotates the motor 31 and moves the support member 29 to a predetermined position. As a result, the first scatterer device 18 is moved to a position corresponding to the position information. The control device 52 confirms based on a detected signal from an encoder, for example, that the support member 29 has reached the predetermined position. That movement of the first scatterer device 18 can be controlled, without always requiring all the items of the above-described irradiation. information, based on at least one of the size of the tumor K, as the irradiation target, in the direction perpendicular to the beam axis m (i.e., the field size or diameter), the position (i.e., the maximum field penetration depth or range) of the tumor K in the direction of the beam axis (depth direction), and the size of the tumor K in the direction of the beam axis (depth direction).

When the second scatterer device 19A is selected in accordance with the treatment plan information, the irradiation controller 50 outputs, to the control device 53, a second scatterer identification signal indicating a desired one of the second scatterers 32, and when the second scatterer device 19B is selected, the irradiation controller 50 outputs, to the control device 54, a second scatterer identification signal indicating a desired one of the second scatterers 36. In other words, when a large irradiation field (e.g., field size φ=350 mm in the data example listed in Table 1) is to be formed for the patient 15 who is going to receive irradiation of the ion beam, the second scatterer identification signal is outputted from the irradiation controller 50 to the control device 53, and when a small irradiation field (e.g., field size φ=200 mm or 60 mm in the data example listed in Table 1) is to be formed, the second scatterer identification signal is outputted from the irradiation controller 50 to the control device 54. Upon input of the second scatterer identification signal, the control device 53 (or the control device 54) sets a rotational angle of the table 33 (or the table 37) in accordance with the input second scatterer identification signal, and moves the table moving device 34 (or the table moving device 38). As a result, the table 33 (or the table 37) is rotated so that the second scatterer 32 (or the second scatterer 36) (which is adapted for the field size to be formed) corresponding to the second scatterer identification signal is moved to locate on the beam axis m (at the ion beam passage position). With the rotation of the table 33, the second scatterer 32 is located on the beam axis m at a first position downstream of the first scatterer 28 in the direction of travel of the ion beam. With the rotation of the table 37, the second scatterer 36 is located on the beam axis m at a second position downstream of both the first scatterer 28 and the first position in the direction of travel of the ion beam.

At the same time, a blank port identification signal is outputted from the irradiation controller 50 to the control device 54 (or the control device 53) to which the second scatterer identification signal has not been inputted. Upon input of the blank port identification signal, the control device 54 (or the control device 53) sets a rotational angle of the table 37 (or the table 33) correspondingly and moves the table moving device 38 (or the table moving device 34). As a result, the table 33 (or the table 37) is rotated so that the blank port 37a (or the blank port 33a) of the table 37 (or the table 33) is moved to position on the beam axis m.

Further, depending on the irradiation conditions described above, the irradiation controller 50 outputs an identification signal indicating the type of the SOBP producing device 20 to the control device 55 along with a command signal. In accordance with the identification signal, the control device 55 selects one of the plurality of wedge structures 39A, 39B and 39C mounted on the table 40 as shown in FIG. 4, which is adapted to enlarge the dose distribution by a setting value in the direction of travel of the ion beam. The table 40 is translated by the moving device 41 on a plane perpendicular to the direction of travel of the ion beam to be positioned on the beam axis m.

Moreover, depending on the irradiation conditions described above, the irradiation controller 50 outputs information indicating the thickness of the range adjustment device 21 to the control device 56 along with a command signal. In accordance with the thickness information, the control device 56 operates the block moving devices 43, 43 and translates the blocks 42A, 42B to predetermined positions so that the overlapped portion of the wedge-shaped blocks 42A, 42B has a thickness corresponding to the setting value on the beam axis m.

After the selected scatterers and energy absorber have been set at the ion beam passage position (on the beam axis m) and the first scatterer device 18 has been moved to the predetermined position as described above, preparations required before the treatment, such as adjustment of the ion beam is carried out.

Subsequently, the bolus 25 for the patient 15 is installed in a bolus holder provided in the casing 16, and the patient collimator 26 is installed within the casing 16 at a position below the bolus holder. The bolus 25 and the patient collimator 26 are made of an ion beam shielding material, such as chemical wood or brass, and are formed in match with the tumor shape outputted from the treatment planning device 58. The bolus 25 is formed by high precision processing to be three-dimensionally matched with the shape of deepest portion of the tumor in the direction of travel of the ion beam, and it is exchanged per shot of irradiation. The patient collimator 26 is formed by high precision processing to be matched with the projected shape of the tumor on a plane perpendicular to the direction of travel of the ion beam, and it is exchanged per shot of irradiation.

After the completion of the preparations described above, the treatment couch 14 is moved so that the tumor K in the body of the patient 15 is aligned with the beam axis m of the irradiation nozzle 100. The treatment is then started. An operator inputs a treatment start signal from a control panel (not shown). An accelerator controller (not shown) starts operation in response to the treatment start signal, and the ion beam accelerated up to a desired level of energy with the operation of the accelerator controller is extracted from the synchrotron 4.

The extracted ion beam reaches the irradiation nozzle 100 and travels inside the irradiation nozzle 100 along the beam axis m as described above. More specifically, the ion beam is scattered while passing the first scatterer 28 and the second scatterer 32 (or 36), whereby the ion beam is spread into a conical shape in the direction of travel of the ion beam. Then, the ion beam passes the SOBP producing device 20. Because the wedge-shaped member 39a in the SOBP producing device 20 has different values of thickness in the direction of travel of the ion beam as described above, the ion beam energy is attenuated at different rates depending on the passage regions, and Bragg peaks are formed at different positions in the patient body. As a result, the dose distribution in the direction of travel of the ion beam is flattened. Thereafter, the ion beam passes the wedge-shaped blocks 42A, 42B of the range adjustment device 21 while the ion beam energy is reduced by the wedge-shaped blocks 42A, 42B for adjustment of the ion beam range in the patient body.

The ion beam having passed the range adjustment device 21 then passes the bolus 25. The range of the ion beam is adjusted by the bolus 25 in match with the shape of the tumor K in the direction of travel of the ion beam. A portion of the ion beam having passed the bolus 25, which is positioned outside the shape of the tumor K projected in the direction of the beam axis m is eliminated by the patient collimator 26. In other words, the patient collimator 26 allows only the ion beam positioned inside the collimator shape to pass through it. The ion beam having passed the patient collimator 26 is irradiated to the tumor K while forming a high dose region concentrated in a tumor area to be treated.

The effects and advantages of the particle beam irradiation equipment of this embodiment operating in such a manner with the above-described construction will be described below.

(1) Effects of Providing Long Range and Dose Uniformity

Figure 5A:
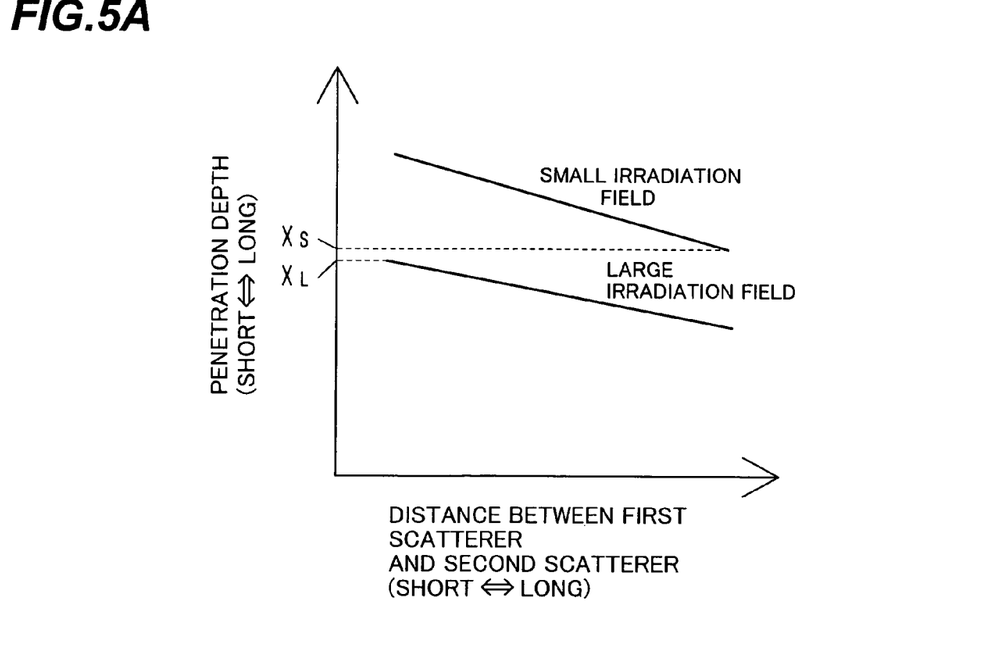
FIGS. 5A and 5B are graphs showing respectively the relationships of a penetration range and uniformity in dose distribution with respect to the distance between a first scatterer and a second scatterer when the position of the first scatterer is fixed.

In the double scattering method, as described before, arranging the scatterers at positions as near as possible to the most upstream side is effective in decreasing the thickness of each of the first and second scatterers to reduce the range loss, and in extending the range to increase the penetration depth in the patient body. While the first scatterer is usually arranged near the most upstream side in the irradiation nozzle, the second scatterer is also preferably arranged, from the standpoint of increasing the range length, at a position as near as possible to the most upstream side so that the distance between the first and second scatterers is minimized. Further, the nearer the second scatterer is positioned to the irradiation target, the lower is the sharpness of a penumbra of the ion beam after being cut by the collimator. From this point of view, too, the second scatterer is preferably arranged at a position as near as possible to the most upstream side. FIG. 5A is a graph showing the relationship between the range (penetration depth) and the distance from the second scatterer to the first scatterer when the position of the first scatterer is fixed. As seen from the graph, the range length is increased as the distance between the second scatterer and the first scatterer decreases.

Figure 5B:
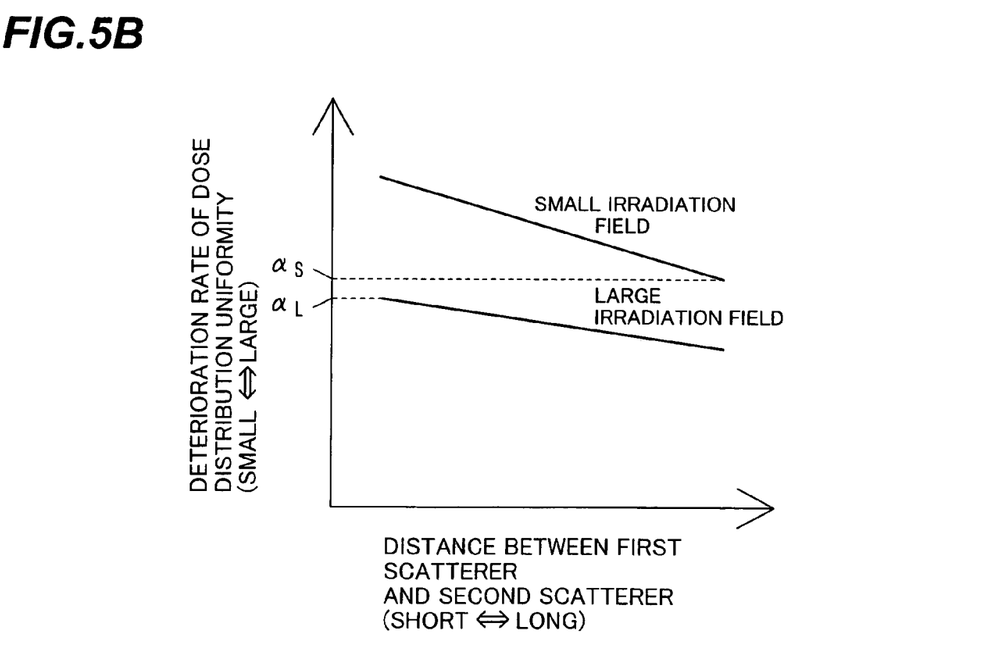

On the other hand, in the double scattering method, if a deviation occurs between an axis along which the ion beam travels and the center position of the second scatterer, dose uniformity in irradiation to the tumor K deteriorates depending on the deviation to a larger extent as the distance between the first and second scatterers decreases. From the standpoint of improving dose uniformity in irradiation to the tumor K (i.e., dose uniformity), therefore, the second scatterer is preferably arranged at a position as near as possible to the most downstream side so that the distance between the first and second scatterers is maximized. FIG. 5B is a graph showing the relationship between a deterioration rate of uniformity in dose distribution per unit deviation and the distance from the second scatterer to the first scatterer when the position of the first scatterer is fixed. As seen from the graph, the dose uniformity deterioration rate is decreased (uniformity of the irradiation dose is improved) as the distance between the second scatterer and the first scatterer increases.

Considering, for example, the case of increasing the practically formable maximum field size in conformity with recent demands in medical applications, however, there is a large difference in characteristics between when a comparatively large irradiation field is formed and when a comparatively small irradiation field is formed, as plotted in FIGS. 5A and 5B.

More specifically, looking at deterioration of the dose uniformity plotted in FIG. 5B, when a comparatively large irradiation field is formed, a slight deviation between the axis along which the ion beam travels and the center position of the second scatterer causes a small influence upon the large irradiation field and hence the resulting influence is mostly absorbed on the whole, even if the slight deviation occurs. A value of the dose uniformity deterioration rate in this case is smaller than that in the case of forming a comparatively small irradiation field. On the other hand, looking at the range plotted in FIG. 5A, when a comparatively small irradiation field is formed, the ion beam is more densely concentrated in the small irradiation field, thus resulting in a longer range and a larger penetration depth than when a comparatively large irradiation field is formed.

As seen from the results mentioned above, when a large irradiation field is formed, the distance between the second scatterer and the first scatterer is preferably set to be small for the reason that a value of the dose uniformity deterioration rate is relatively small in nature and hence importance should be placed on the range even with a slight deterioration of the dose uniformity from the view point of balance between a longer range and higher dose uniformity. Conversely, when a small irradiation field is formed, the distance between the second scatterer and the first scatterer is preferably set to be large for the reason that the range is relatively long in nature and hence importance should be placed on the dose uniformity even with a slight reduction of the range from the view point of balance between a longer range and higher dose uniformity.

In the irradiation nozzle 100 provided in the particle beam irradiation equipment of this embodiment, based on the above-described review, when the field size is large (e.g., field size $\phi$=350 mm), the table moving device 34 is controlled by the control device 53 to rotate the table 33 so that one of the second scatterers 32a to 32e on the table 33 is positioned on the beam axis m. At this time, the table 37 is rotated to position the blank port 37a on the beam axis m. Also, when the field size is small (e.g., field size $\phi$=200 mm or 60 mm), the table moving device 38 is operated by the control device 54 to rotate the table 37 so that one of the second scatterers 36a to 36e on the table 37 is positioned on the beam axis m. At this time, the table 33 is rotated to position the blank port 33a on the beam axis m.

With such setting, when a large irradiation field is formed, the ion beam is irradiated in accordance with the characteristics plotted in relatively left-side regions in FIGS. 5A and 5B. As indicated by, e.g., $X_L$ in FIG. 5A, a long range can be obtained with a reduction of range loss. Consequently, as seen from FIG. 5A, the range length can be increased to a level comparable to a minimum value $X_S$ of the range obtained in the case of forming a small irradiation field. On this occasion, the deterioration rate of the dose uniformity is relatively increased as indicated by, e.g., $\alpha_L$ in FIG. 5B. In spite of such an increase, as seen from FIG. 5B, the deterioration rate of the dose uniformity can be held at a level comparable to a minimum value $\alpha_S$ of the deterioration rate obtained in the case of forming a small irradiation field.

On the other hand, when a small irradiation field is formed, the ion beam is irradiated in accordance with the characteristics plotted in relatively right-side regions in FIGS. 5A and 5B. The deterioration rate of the dose uniformity can be reduced as indicated by, e.g., $\alpha_s$ in FIG. 5B. Consequently, as seen from FIG. 5B, the dose uniformity can be improved to a level comparable to a maximum value $\alpha_L$ of the deterioration rate obtained in the case of forming a large irradiation field. On this occasion, the range is relatively decreased to, e.g., $X_S$ in FIG. 5A. In spite of such a decrease, as seen from FIG. 5A, the range can be held at a level comparable to a maximum value $X_L$ of the range obtained in the case of forming a large irradiation field.

Thus, with this embodiment, regardless of whether a large irradiation field or a small irradiation field is formed, the range can be held at a comparatively large value as indicated by $X_L$ or $X_S$ and prevented from shortening from such a level, while the deterioration rate of the dose uniformity can be held at a comparatively small value as indicated by $\alpha_S$ or $\alpha_L$ and prevented from increasing from such a level. In other words, irrespective of the field size, the second scatterer can be placed at an optimum position in consideration of balance between a longer range and higher dose uniformity. As a result, the irradiation can always be realized at a long range and high dose uniformity over the whole of the practically formable irradiation field.

(2) Further Improvement of Dose Uniformity

In this embodiment, in addition to the selective use of the second scatterer 32 or 36 depending on the field size, the first scatterer device 18 is movable in the direction of travel of the ion beam. Therefore, the scattering profile size of the ion beam (i.e., the size of the ion beam spread out in a direction perpendicular to the direction of travel of the ion beam) can be finely adjusted at the position of the tumor K. Stated another way, the scattering profile size decreases with the first scatterer 28 positioned closer to the tumor K, and conversely it increases with the first scatterer 28 positioned farther way from the tumor K. With such a movement of the first scatterer 28, the ion beam can be adjusted to the optimum scattering profile size without changing the range of the ion beam in the body of the patient 15, while the dose distribution in the direction of travel of the ion beam is flattened. As a result, the dose distribution irradiated to the tumor K can be finely adjusted. In practice, when the scattering profile size of the ion beam is smaller than the optimum size, the first scatterer 28 is moved to position farther way from the tumor K, and conversely when it is larger than the optimum size, the first scatterer 28 is moved to position closer to the tumor K. Thus, with this embodiment, the dose distribution in the tumor K can be made more uniform.

(3) In this embodiment, with the functions of the control system, especially the functions of the irradiation controller 50 and the control devices 53, 54, the second scatterer 32 and the second scatterer 36 can be easily positioned in the ion beam passage region at positions different from each other in the direction of travel of the ion beam. In particular, since the irradiation controller 50 selects the position in the direction of travel of the ion beam (first or second position, more specifically the table 33 or 37), at which the second scatterer is to be positioned, by using the treatment plan information for the patient 15, i.e., the field size (irradiation field information), the second scatterer can be positioned at a desired position corresponding to the relevant patient 15. It is hence possible to easily produce the ion beam corresponding to the scattering profile size required for the relevant patient 15, and to obtain a uniform dose distribution.

Additionally, note that in order to provide only the above (1) of the essential effects of this embodiment, the first scatterer device 18 is not always required to be movable in the direction of the beam axis m, and it may be of a fixed structure.

Furthermore, while, in this embodiment, the second scatterer device 19A and the second scatterer device 19B are provided in two stages and are selectively used depending on the field size, the present invention is not limited to such an arrangement. As an alternative, other one or more second scatterer devices for medium field size may be disposed between the second scatterer devices 19A and 19B to constitute three, four or more stages for finer selection. In other words, it is just essential that, for the purpose of forming the irradiation fields having sizes different from each other, plural stages of second scatterer devices are disposed downstream of the first scatterer device 18 in the direction of travel of the ion beam at the spacing depending on the difference in the field size.

Second Embodiment

Particle beam irradiation equipment (particle beam treatment equipment) according to a second embodiment of the present invention will be described below. In the particle beam irradiation equipment of this second embodiment, the irradiation nozzle 100 in the particle beam irradiation equipment 1 shown in FIG. 1 is replaced with an irradiation nozzle 100A shown in FIG. 6.

Figure 6:
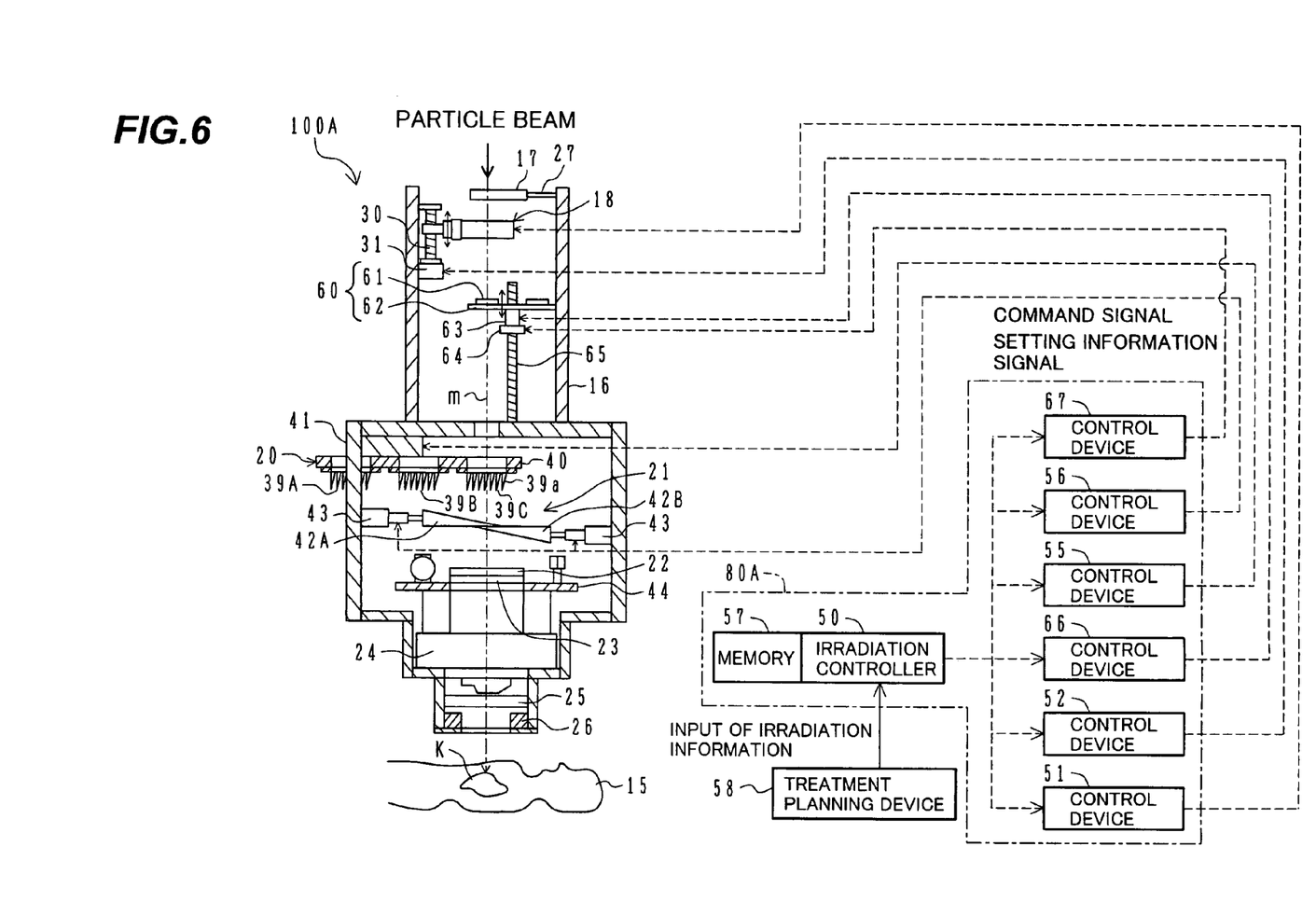
FIG. 6 is a vertical sectional view showing a detailed construction of irradiation field producing equipment provided in particle beam irradiation equipment according to a second embodiment of the present invention.

In FIG. 6, the irradiation nozzle 100A includes one unit of second scatterer device 60, which is movable in the direction of the beam axis m, in stead of the two-stage second scatterer devices 19A, 19B which are fixed at respective upstream and downstream positions in spaced relation. The irradiation nozzle 100A further includes a second scatterer moving device 64.

The second scatterer device 60 is adapted for both the cases of a large field size and a small field size (i.e., usable regardless of the field size), and includes second scatterers 61. Similarly to the second scatterers 32 and 36 in the first embodiment, a plurality of second scatterers 61 are circumferentially disposed on a scatterer mount table 62 having a circular (or substantially disk-like) shape. A detailed structure of the second scatterer device 60 will be described below with reference to FIG. 7. The plurality of second scatterers 61 include two sets of plural second scatterers 32 and 36. In addition, the second scatterer device 60 includes a disk-shaped support member 73 and a tubular support member 68. One end of the tubular support member 68 is mounted to the table 62. The other end of the tubular support member 68 is rotatably held within a retainer 72 mounted to the support member 73. A ball screw 65 having a lower end mounted to a horizontal wall portion of the casing 16 penetrates through the support member 73, the tubular support member 68, and the table 62. The table 62 is rotatable about the ball screw 65 together with the tubular support member 68. The ball screw 65 is extended in parallel to the beam axis m.

Figure 7:
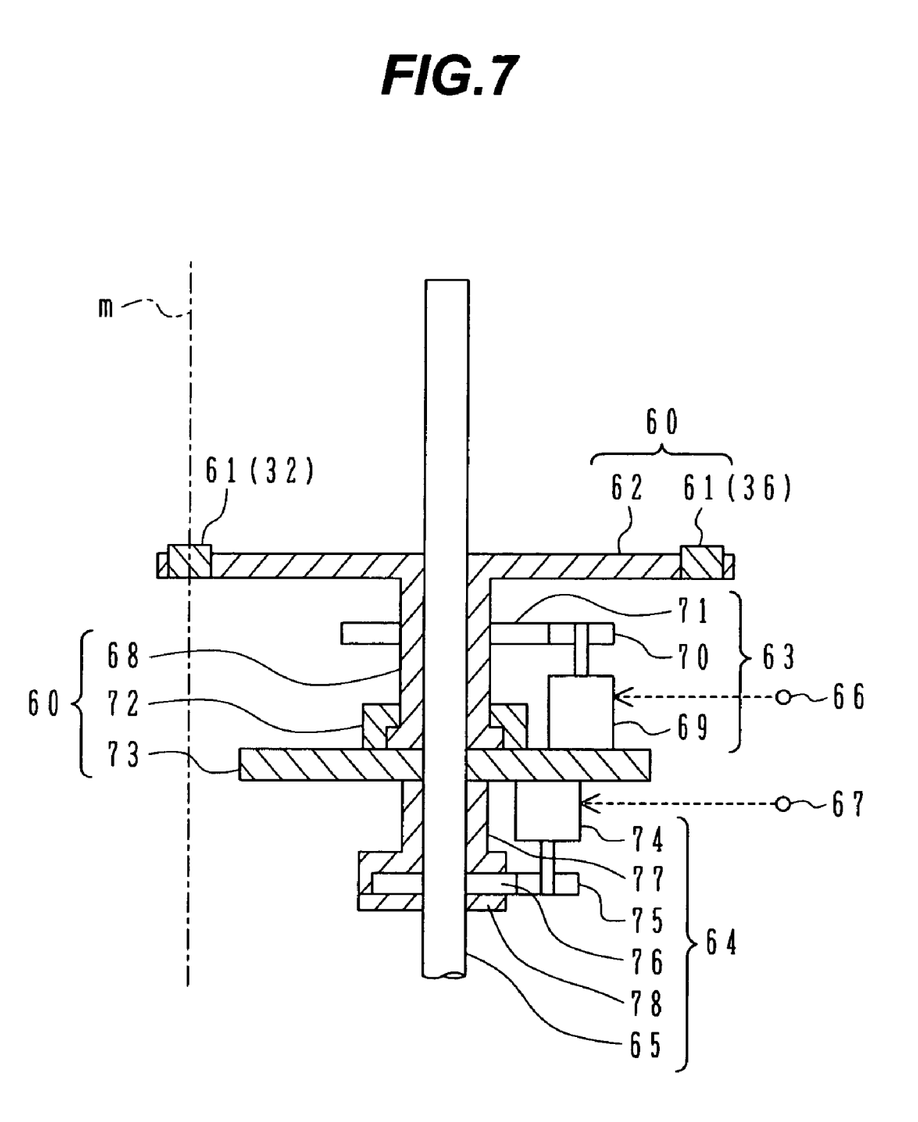
FIG. 7 is a vertical sectional view showing a detailed structure of a second scatterer device, a table moving device, and a second scatterer moving device shown in FIG. 6.

A table moving device 63 comprises a motor 69 and gears 70, 71. The motor 69 is mounted to the support member 73. The gear 70 attached to a rotary shaft of the motor 69 meshes with the gear 71, which is attached to the tubular support member 68, while the tubular support member 68 penetrates the gear 71. Rotating forces of the motor 69 are transmitted to the gear 71 through the gear 70 to rotate the tubular support member 68, thereby rotating the table 62. Thus, with the table 62 rotated by the table moving device 63, one of the plurality of second scatterers 61 is selected and positioned on the beam axis m for performing irradiation at high efficiency and high accuracy. The second scatterer device 60, specifically the support member 73, is allowed to move only in the direction parallel to the beam axis m under guide of a guide unit (not shown) fixed to the casing 16, while it is restricted from rotating about the ball screw 65 by the guide unit.

A second scatterer moving device (linear actuator) 64 comprises a motor (e.g., an AC servo motor or a stepping motor) 74, a gear 75, a nut member 76, and a nut holder 77. The motor 74 and the nut holder 77 are mounted to a surface of the support member 73 opposed to the surface to which the motor 69 is mounted. The ball screw 65 penetrates the nut holder 77. The nut member 76 meshes with the ball screw 65. The nut member 76 is positioned in a lower end portion of the nut holder 77 and is rotatably disposed between the nut holder 77 and a retainer 78 attached to the nut holder 77. The gear 75 attached to a rotary shaft of the motor 74 meshes with a gear formed around the nut member 76. Further, an encoder (not shown) is coupled to the rotary shaft of the motor 74.

The particle beam treatment equipment of this embodiment includes a control system 80A comprising an irradiation controller 50 and control devices 51, 52, 55, 56, 66 and 67. The control devices 66, 67 are provided in place of the control devices 53, 54 in the first embodiment.

The control device 66 has the functions similar to those of the control devices 53, 54 in the first embodiment. More specifically, by employing the irradiation condition information stored in the memory 57, the irradiation controller 50 selects a desired one of the second scatterers 61 based on the irradiation condition information that is listed, by way of example, in Table 1 and is also stored in the memory 57 in advance. Upon input of a second scatterer identification signal indicating the selected second scatterer 61 from the irradiation controller 50, the control device 66 sets a rotational angle of the table 62 in accordance with the input second scatterer identification signal, and rotates the motor 69 of the table moving device 63. As a result, the table 62 is rotated so that the second scatterer 61 corresponding to the second scatterer identification signal is moved to locate on the beam axis m.

Meanwhile, among the items of the irradiation condition information stored in the memory 57, "the type of the second scatterer mount table (i.e., SC2 table)" in the irradiation condition information listed in Table 1 is replaced with "the position of the second scatterer (i.e., SC2 position)". The irradiation controller 50 outputs, to the control device 67, second scatterer position information indicating the position of the second scatterer selected based on the treatment plan information for the patient 15. In accordance with the second scatterer position information, the control device 67 operates the second scatterer moving device 64 so that the table 62 is moved to the second scatterer position. More specifically, the control device 67 rotates the motor 74. Rotating forces of the motor 74 are transmitted to the nut member 76 through the gear 75. The nut member 76 meshing with the ball screw 65 and positioned between the nut holder 77 and the retainer 78 is thereby moved in the axial direction of the ball screw 65, whereupon the nut holder 77, the support member 73, the tubular support member 68, and the table 62 are also moved in the axial direction of the ball screw 65. As a result, the table 62 is moved to a position corresponding to the second scatterer position information (i.e., the second scatterer position). The control device 67 stops the rotation of the motor 74 when it is confirmed, for example, based on a detected signal from the encoder that the table 62 has reached the second scatterer position.

When the field size required for the irradiation to the patient 15 is large (e.g., field size φ=350 mm in the data example listed in Table 1), the table 62 of the second scatterer device 60 is moved under the above-mentioned control of the control device 67 to the position of the table 33 of the second scatterer device 19A in the first embodiment (i.e., first setting position). Also, when the required field size is small (e.g., field size φ=200 mm or 60 mm in the data example listed in Table 1), the table 62 of the second scatterer device 60 is moved under the above-mentioned control of the control device 67 to the position of the table 37 of the second scatterer device 19B in the first embodiment (i.e., second setting position).

The second scatterer 61 to be positioned on the beam axis m in accordance with the second scatterer identification signal is selected as the second scatterer 32 when the field size is large (e.g., field size φ=350 mm), and as the second scatterer 36 when the field size is small (e.g., field size φ=200 mm or 60 mm).

This second embodiment can provide the same effects as those obtainable with the first embodiment. In addition, this second embodiment is capable of constructing the second scatterer device in more compact size than in the first embodiment, and simplifying the construction of the irradiation nozzle.

In the irradiation nozzle 100A provided in the particle beam irradiation equipment of this embodiment, as described above, when the field size is large (e.g., field size φ=350 mm), the motor 64 is rotated by the control device 67 and the second scatterer device 60 is moved to the upstream side. When the field size is small (e.g., field size φ=200 mm or 60 mm), the second scatterer device 60 is moved to the downstream side. As in the first embodiment, therefore, irrespective of the field size, the second scatterer can be placed at an optimum position in consideration of balance between a longer range and higher dose uniformity. As a result, the irradiation can always be realized at a long range and high dose uniformity over the whole of the formable irradiation field. Further, since the first scatterer device 18 is movable in the direction of transfer of the ion beam, the dose distribution in the tumor K can be made more uniform.

In the first and second embodiments, a cyclotron may be used as the charged particle beam accelerator in place of the synchrotron.

According to the present invention, a long range of a charged particle beam can be obtained in the patient body and dose uniformity in irradiation can be ensured at any field size.

What is claimed is:

1. Particle beam irradiation equipment comprising charged particle beam generation equipment and a charged particle beam irradiation nozzle for irradiating a charged particle beam extracted from said charged particle beam generation equipment to an irradiation target,
   wherein said charged particle beam irradiation nozzle comprises:
   a first scatterer device including a first scatterer through which said charged particle beam passes;
   a second scatterer device including a plurality of second scatterers through which an unoccluded Gaussian distributed charged particle beam passes after having passed said first scatterer, said second scatterer device causing one of said plurality of second scatterers to position in a passage region of said charged particle beam at one of plural different positions in the direction of travel of said charged particle beam; and a collimator for shaping said charged particle beam, said plurality of second scatterers of the second scatterer device each being configured to have higher scatter strength in the central side than in the radially outer peripheral side to provide a beam irradiation of a double scattering method in combination with said first scatterer of the first scatterer device, said plurality of second scatterers including a second scatterer for smaller irradiation field size caused to position in said passage region at a first position in the direction of travel of said charged particle beam and used when said collimator is adapted for a relatively small first irradiation field and another second scatterer for larger irradiation field size caused to position in said passage region at a second position upstream of said first position in the direction of travel of said charged particle beam and used when said collimator is adapted for a larger second irradiation field than said first irradiation field, said second scatterer for smaller irradiation field size caused to position in the passage region at said first position having a thickness different from that of said another second scatterer for larger irradiation field caused to position in the passage region at said second position so as to provide smaller scattering strength of said charged particle beam in a direction perpendicular to the direction of travel of said charged particle beam than said another second scatterer for larger irradiation field size.

2. Particle beam irradiation equipment comprising charged particle beam generation equipment and a charged particle beam irradiation nozzle for irradiating a charged particle beam extracted from said charged particle beam generation equipment to an irradiation target, wherein said charged particle beam irradiation nozzle comprises a first scatterer device including a first scatterer through which said charged particle beam passes, a second scatterer device including a plurality of second scatterers through which an unoccluded Gaussian distributed charged particle beam passes, said plurality of second scatterers being to-be-positioned in a passage region of said charged particle beam after having passed said first scatterer, and a collimator for shaping said charged particle beam; and said particle beam irradiation equipment includes a control system for controlling said second scatterer device such that one of said plurality of second scatterers is positioned in said passage region at one of plural different positions in the direction of travel of said charged particle beam, said plurality of second scatterers of the second scatterer device each being configured to have higher scatter strength in the central side than in the radially outer peripheral side to provide a beam irradiation of a double scattering method in combination with said first scatterer of the first scatterer device, said plurality of second scatterers including a second scatterer for smaller irradiation field size caused to position in said passage region at a first position in the direction of travel of said charged particle beam and used when said collimator is adapted for a relatively small first irradiation field and another second scatterer for larger irradiation field size caused to position in said passage region at a second position upstream of said first position in the direction of travel of said charged particle beam and used when said collimator is adapted for a larger second irradiation field than said first irradiation field, said second scatterer for smaller irradiation field size caused to position in the passage region at said first position having a thickness different from that of said another second scatterer for larger irradiation field caused to position in the passage region at said second position so as to provide smaller scattering strength of said charged particle beam in a direction perpendicular to the direction of travel of said charged particle beam than said another second scatterer for larger irradiation field size.

3. Particle beam irradiation equipment according to claim 2, wherein said control system places the one of said plurality of second scatterers at the one of the plural different positions selected based on treatment plan information.

4. Particle beam irradiation equipment according to claim 3, wherein said treatment plan information is irradiation field information.

5. Particle beam irradiation equipment according to claim 3, wherein said control system places, at the selected position, the one of said plurality of second scatterers selected based on another treatment plan information.

6. Particle beam irradiation equipment according to claim 5, wherein said another treatment plan information is energy information of an ion beam.

7. Particle beam irradiation equipment comprising charged particle beam generation equipment and a charged particle beam irradiation nozzle for irradiating a charged particle beam extracted from said charged particle beam generation equipment to an irradiation target, wherein said charged particle beam irradiation nozzle comprises a first scatterer device including a first scatterer through which said charged particle beam passes, an upstream second scatterer device including a second scatterer to be positioned in a passage region of an unoccluded Gaussian distributed charged particle beam at a first position downstream of said first scatterer device in the direction of travel of said charged particle beam, a downstream second scatterer device including another second scatterer to be positioned in said passage region at a second position downstream of said first position in the direction of travel of said unoccluded Gaussian distributed charged particle beam; and a collimator for shaping said charged particle beam; and said second scatterer of each of said upstream and downstream second scatterer device being configured to have higher scatter strength in the central side than in the radially outer peripheral side to provide a beam irradiation of a double scattering method in combination with said first scatterer of the first scatterer device, said second scatterer of said upstream second scatterer device being used as one for larger irradiation field size when said collimator is adapted for a larger second irradiation field than a first irradiation field, and said second scatterer of said downstream second scatterer device being used as one for smaller irradiation field size when said collimator is adapted for said first irradiation field, said second scatterer of said downstream second scatterer device for smaller irradiation field size having a thickness different from that of said second scatterer of said upstream second scatterer device for larger irradiation field size so as to provide smaller scattering strength of said charged particle beam in a direction perpendicular to the direction of travel of said charged particle beam than said second scatterer of said upstream second scatterer device for larger irradiation field size.

8. Particle beam irradiation equipment according to claim 7, further comprising a control system for controlling a selected one of said upstream second scatterer device and said downstream second scatterer device such that the second scatterer included in said selected second scatterer device is positioned in said passage.

9. Particle beam irradiation equipment according to claim 8, wherein said control system selects the one of said second scatterers devices based on treatment plan information.

10. Particle beam irradiation equipment according to claim 8, wherein said upstream second scatterer device includes a first table for mounting said second scatterer thereon and positioning said second scatterer in said passage region, and said downstream second scatterer device includes a second table for mounting said another second scatterer thereon and positioning said another second scatterer in said passage region.

11. Particle beam irradiation equipment according to claim 10, wherein said first table mounts said second scatterer in plural number thereon, said second table mounts said another second scatterer in plural number thereon, and said another second scatterer mounted in plural number on said second table provides smaller scattering strength of said charged particle beam in a direction perpendicular to the direction of travel of said charged particle beam than said second scatterer mounted in plural number on said first table.

12. Particle beam irradiation equipment according to claim 10 or 11, wherein said charged particle beam irradiation nozzle further comprises a first table moving device for moving said first table in the direction perpendicular to the direction of travel of said charged particle beam, and a second table moving device for moving said second table in the direction perpendicular to the direction of travel of said charged particle beam; and said control system controls the table moving device included in the selected second scatterer device, thereby controlling movement of the corresponding table such that the corresponding second scatterer is positioned said passage region.

13. Particle beam irradiation equipment comprising charged particle beam generation equipment and a charged particle beam irradiation nozzle for irradiating a charged particle beam extracted from said charged particle beam generation equipment to an irradiation target, wherein said charged particle beam irradiation nozzle comprises: a first scatterer through which said charged particle beam passes; a first table disposed downstream of said first scatterer in the direction of travel of said charged particle beam and mounting a second scatterer, wherein said first table is to be positioned in a passage region of said charged particle beam;

a second table disposed downstream of said first table in the direction of travel of said charged particle beam and mounting another second scatterer, wherein said second table is to be positioned in said passage region; and a collimator for shaping said charged particle beam; said second scatterer of each of the first and second tables being configured to have higher scatter strength in the central side than in the radially outer peripheral side to provide a beam irradiation of a double scattering method in combination with said first scatterer, said second scatterer mounted on said first table being used as one for larger irradiation field size when said collimator is adapted for a larger second irradiation field than a first irradiation field, and said another second scatterer mounted on said second table being used as one for smaller irradiation field size when said collimator is adapted for said first irradiation field, said another second scatterer for smaller irradiation field size mounted on said second table having a thickness different from that of said second scatterer for larger irradiation field mounted on said first table so as to provide smaller scattering strength of said charged particle beam in a direction perpendicular to the direction of travel of said charged particle beam than said second scatterer for larger irradiation field size~ and wherein said second scatterer device modulates an unoccluded Gaussian distributed charged particle beam.

14. Particle beam irradiation equipment according to claim 13, wherein said first scatterer is movable within said charged particle beam irradiation nozzle in the direction of travel of said charged particle beam.

15. Particle beam irradiation equipment according to claim 14, further comprising a first scatterer moving device for moving said first scatterer in the direction of travel of said charged particle beam, and a first scatterer control device for controlling said first scatterer moving device, thereby controlling an amount by which said first scatterer is to be moved.

16. Particle beam irradiation equipment according to claim 13, wherein said first table and said second table are capable of placing respectively said second scatterer and said another second scatterer in said passage region.

17. Particle beam irradiation equipment according to claim 16, further comprising a first table moving device for moving said first table in the direction perpendicular to the direction of travel of said charged particle beam, a second table moving device for moving said second table in the direction perpendicular to the direction of travel of said charged particle beam, and a table control device for controlling the table moving device to move a selected one of said first and second tables, thereby controlling movement of the selected table.

18. Particle beam irradiation equipment comprising charged particle beam generation equipment and a charged particle beam irradiation nozzle for irradiating a charged particle beam extracted from said charged particle beam generation equipment to an irradiation target, wherein said charged particle beam irradiation nozzle comprises:

a first scatterer device including a first scatterer through which said charged particle beam passes;

a second scatterer device including a plurality of second scatterers to be positioned in a passage region of an unoccluded Gaussian distributed charged particle beam resulting from passage through first scatterer, said second scatterer device being movably disposed in the direction of travel of said charged particle beam; and a collimator for shaping said charged particle beam, said plurality of second scatterers of the second scatterer device each being configured to have higher scatter strength in the central side than in the radially outer peripheral side to provide a beam irradiation of a double scattering method in combination with said first scatterer of the first scatterer device, said plurality of second scatterers comprising a second scatterer for larger irradiation field size caused to position in said passage region of the charged particle beam at a first position included in plural different positions in the direction of travel of said charged particle beam and used when said collimator is adapted for a larger second irradiation field than a first irradiation field, and another second scatterer for smaller irradiation field size caused to position in said passage region at a second position downstream of said first position included in said plural different positions and used when said collimator is adapted for said first irradiation field, said another second scatterer for smaller irradiation field size caused to position in said passage region at said second position having a thickness different from that of said second scatterer for larger irradiation field size caused to position in said passage region at said first position so as to provide smaller scattering strength of said charged particle beam in a direction perpendicular to the direction of travel of said charged particle beam than said second scatterer for larger irradiation field size caused to position in said passage region at said first position.

19. Particle beam irradiation equipment according to claim 18, further comprising a second scatterer moving device for moving said second scatterer device in the direction of travel of said charged particle beam, and a second scatterer control device for controlling said second scatterer moving device, thereby controlling an amount by which said second scatterer device is to be moved.

20. Particle beam irradiation equipment according to any of claim 1, 7, 8, and 18, wherein said first scatterer device is movable in the direction of travel of said charged particle beam.

21. Particle beam irradiation equipment according to claim 20, further comprising a first scatterer moving device for moving said first scatterer device in the direction of travel of said charged particle beam, and a first scatterer control device for controlling said first scatterer moving device, thereby controlling an amount by which said first scatterer device is to be moved.

22. Particle beam irradiation equipment according to claim 18, wherein said second scatterer device comprises a table for positioning said second scatterer in said passage region, and a table moving device for moving said table in the direction perpendicular to the direction of travel of said charged particle beam.

23. Particle beam irradiation equipment according to claim 22, further comprising a table control device for controlling said table moving device, thereby controlling movement of said table.

24. A particle beam irradiation method using a charged particle beam irradiation nozzle comprising a first scatterer through which a charged particle beam passes, a plurality of second scatterers through which an unoccluded Gaussian distributed charged particle beam passes after having passed said first scatterer, said plurality of second scatterers comprising a second scatterer for larger irradiation field size caused to position in a passage region of said charged particle beam at one position included in plural different positions in the direction of travel of said charged particle beam, and another second scatterer for smaller irradiation field size caused to position in said passage region at another position downstream of said one position included in said plural different positions, and a collimator for shaping said charged particle beam, said plurality of second scatterers each being configured to have higher scatter strength in the central side than in the radially outer peripheral side to provide a beam irradiation of a double scattering method in combination with said first scatterer of the first scatterer device, said another second scatterer for smaller irradiation field size caused to position in said passage region at said another position having a thickness different from that of said second scatterer for larger irradiation field size caused to position in said passage region at said one position so as to provide smaller scattering strength of said unoccluded Gaussian distributed charged particle beam in a direction perpendicular to the direction of travel of said unoccluded Gaussian distributed charged particle beam than said second scatterer for larger irradiation field size caused to position in said passage region at said one position,~ comprising the steps of:

placing said second scatterer for larger irradiation field size in said passage region of said unoccluded Gaussian distributed charged particle beam at said one position when said collimator is adapted for a larger second irradiation field than a first irradiation field, and irradiating said charged particle beam after having passed said first scatterer and said second scatterer positioned at said one position; and placing said another second scatterer for smaller irradiation field size in said passage region of said unoccluded Gaussian distributed charged particle beam at said another position when said collimator is adapted for said first irradiation field, and irradiating said charged particle beam after having passed said first scatterer and said another second scatterer positioned at said another position.

25. A particle beam irradiation method according to claim 24, wherein said first scatterer is moved in the direction of travel of said charged particle beam.

26. A particle beam irradiation method according to claim 24, wherein said second scatterer is placed at said selected position by moving said second scatterer in the direction of travel of said charged particle beam.

27. A method of adjusting a charged particle beam irradiation nozzle comprising a first scatterer through which a charged particle beam passes, a plurality of second scatterers through which an unoccluded Gaussian distributed charged particle beam passes after having passed said first scatterer, said plurality of second scatterers comprising a second scatterer for larger irradiation field size caused to position in a passage region of said charged particle beam at one position included in plural different positions in the direction of travel of said charged particle beam, and another second scatterer for smaller irradiation field size caused to position in said passage region at another position downstream of said one position included in said plural different positions, and a collimator for shaping said charged particle beam, said plurality of second scatterers each being configured to have higher scatter strength in the central side than in the radially outer peripheral side to provide a beam irradiation of a double scattering method in combination with said first scatterer of the first scatterer device, said another second scatterer for smaller irradiation field size caused to position in said passage region at said another position having a thickness different from that of said second scatterer for larger irradiation field size caused to position in said passage region at said one position so as to provide smaller scattering strength of said charged particle beam in a direction perpendicular to the direction of travel of said charged particle beam than said second scatterer for larger irradiation field size caused to position in said passage region at said one position; comprising the steps of:

placing said second scatterer for larger irradiation field size in said passage region at said one position when said collimator is adapted for a larger second irradiation field than a first irradiation field; and placing said another second scatterer for smaller irradiation field size in said passage region at said another position when said collimator is adapted for said first irradiation field.

28. A method of adjusting a charged particle beam irradiation nozzle comprising a first scatterer through which a charged particle beam passes, a plurality of second scatterers through which an unoccluded Gaussian distributed charged particle beam passes after having passed said first scatterer, said plurality of second scatterers comprising a second scatterer for larger irradiation field size caused to position in a passage region of said charged particle beam at one position included in plural different positions in the direction of travel of said charged particle beam, and another second scatterer for smaller irradiation field size caused to position in said passage region at another position downstream of said one position included in said plural different positions, and a collimator for shaping said charged particle beam, said plurality of second scatterers each being configured to have higher scatter strength in the central side than in the radially outer peripheral side to provide a beam irradiation of a double scattering method in combination with said first scatterer of the first scatterer device, said another second scatterer for smaller irradiation field size caused to position in said passage region at said another position having a thickness different from that of said second scatterer for larger irradiation field size caused to position in said passage region at said one position so as to provide smaller scattering strength of said charged particle beam in a direction perpendicular to the direction of travel of said charged particle beam than said second scatterer for larger irradiation field size caused to position in said passage region at said one position.~ comprising the steps of:

selecting one of said second scatterer for larger irradiation field size and said another second scatterer for smaller irradiation field size depending on the size of the irradiation field size for which said collimator is adapted, and placing the selected second scatterer in said passage region at a selected one of said plural different positions in the direction of travel of said charged particle beam.

29. A method of adjusting a charged particle beam irradiation nozzle according to claim 28, wherein said placing of the selected second scatterer at said selected position is carried out by placing in said passage region the second scatterer included in one of an upstream second scatterer device including said second scatterer for larger irradiation field size to be positioned at said one position downstream of said first scatterer in the direction of travel of said charged particle beam, and a downstream second scatterer device including said another second scatterer for smaller irradiation field size to be positioned in said another position downstream of said upstream second scatterer device.

30. A method of adjusting a charged particle beam irradiation nozzle according to claim 28, wherein said placing of the selected second scatterer at said selected position is carried out by moving said second scatterers in the direction of travel of said charged particle beam.

* * * * *